United States Patent [19]

Grant

[11] Patent Number: 4,874,886

[45] Date of Patent: Oct. 17, 1989

[54] NOVEL FLUORINATED BIS(SALICYLATES)

[75] Inventor: Charles B. Grant, Pittsburg, Calif.

[73] Assignee: The Dow Chemical Company, Midland, Mich.

[21] Appl. No.: 268,118

[22] Filed: Nov. 7, 1988

[51] Int. Cl.$^4$ .............................................. C07C 69/88
[52] U.S. Cl. ...................................... 560/70; 568/416; 560/57; 560/67
[58] Field of Search ............................ 560/70, 67, 57; 558/416

[56] References Cited

U.S. PATENT DOCUMENTS 1,743,635  1/1930  Summers ................................ 560/57

FOREIGN PATENT DOCUMENTS 37-980    12/1958  Japan .
42-1749    1/1967  Japan .
4941430    8/1976  Japan .

Primary Examiner—Paul J. Killos

[57] ABSTRACT

This invention relates to novel fluorinated bis(salicylates). The novel fluorinated bis(salicylates) of this invention are useful as monomers in the synthesis of polymers and copolymers themselves useful as gas separation membrane materials.

12 Claims, No Drawings

NOVEL FLUORINATED BIS(SALICYLATES)

BACKGROUND OF THE INVENTION

This invention relates to novel fluorinated bis(salicylates).

The novel bis(salicylates) of this invention are useful as high temperature stable fluids, starting materials for the formation of fluoroaromatic epoxy resins, and as monomers for the synthesis of fluorinated polymers and copolymers containing said fluorinated bis(salicylates). Useful copolymers containing the novel bis(salicylates) of this invention include copolymers of the fluorinated bis(salicylates) with imides, esters, carbonates, and styrenes. The polymers and copolymers formed from the novel bis(salicylates) of this invention are particularly useful as gas separation membrane materials.

SUMMARY OF THE INVENTION

The invention is a novel fluorinated bis(salicylate) corresponding to the formula:

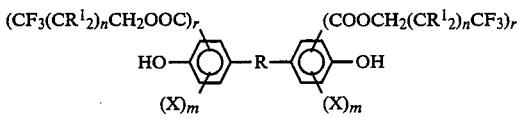

wherein

R is a $C_{1-18}$ divalent hydrocarbon radical, a $C_{1-18}$ divalent inertly substituted hydrocarbon radical, or a $C_{1-18}$ divalent halocarbon radical;

$R^1$ is independently in each occurrence a hydrogen or fluorine;

X is independently in each occurrence hydrogen, a halogen, a $C_{1-3}$ alkyl, a $C_{1-3}$ haloalkyl, or a nitrile;

m is independently in each occurrence an integer between 0 and 3 inclusive;

n is independently in each occurrence an integer between 0 and 6 inclusive; and r is independently in each occurrence an integer between 1 and 4 inclusive.

DETAILED DESCRIPTION OF THE INVENTION

The invention is a novel fluorinated bis(salicylate) corresponding to the formula:

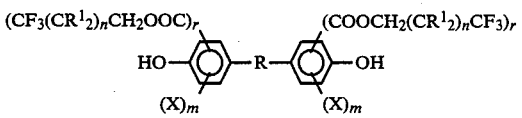

wherein

R is a $C_{1-18}$ divalent hydrocarbon radical, a $C_{1-18}$ divalent inertly substituted hydrocarbon radical, or a $C_{1-18}$ divalent halocarbon radical;

$R^1$ is independently in each occurrence a hydrogen or fluorine;

X is independently in each occurrence hydrogen, a halogen, a $C_{1-3}$ alkyl, a $C_{1-3}$ haloalkyl, or a nitrile;

m is independently in each occurrence an integer between 0 and 3 inclusive;

n is independently in each occurrence an integer between 0 and 6 inclusive; and r is independently in each occurrence an integer between 1 and 4 inclusive.

R is preferably a $C_{1-6}$ divalent hydrocarbon radical, a $C_{1-6}$ divalent inertly substituted hydrocarbon radical, or a $C_{1-6}$ divalent halocarbon radical; R is more preferaly a $C_{1-6}$ divalent hydrocarbon radical or a $C_{1-6}$ divalent fluorocarbon radical, even more preferably a $C_{1-6}$ divalent aliphatic hydrocarbon radical, most preferably a $C_{1-3}$ divalent aliphatic hydrocarbon radical.

$R^1$ is independently in each occurrence preferably hydrogen or fluorine, more preferably fluorine.

X is independently in each occurrence preferably hydrogen, chlorine, bromine, fluorine, methyl, ethyl, trifluoromethyl, or nitrile; X is more preferably hydrogen, fluorine, methyl, ethyl, or trifluoromethyl; X is even more preferably hydrogen, fluorine, or methyl.

m is independently in each occurrence an integer preferably between 0 and 3 inclusive, more preferably between 1 and 3 inclusive, even more preferably between 2 and 3 inclusive.

n is independently in each occurrence an integer preferably between 0 and 6 inclusive, more preferably between 0 and 3 inclusive.

r is independently in each occurrence an integer preferably between 1 and 4 inclusive, more preferably between 1 and 3 inclusive, even more preferably between 1 and 2 inclusive.

The location of the $-COOCH_2(CR^1)_nCF_3$ group is preferably at the 2, 3, or 5 ring positions relative to the bridging group R between the phenol rings, more preferably at the 3 or 5 ring positions relative to the bridging group R between the phenol rings, most preferably at the 5 ring positions relative to the bridging group R between the phenol rings.

The fluorinated bis(salicylates) of this invention may be prepared through esterification of the appropriate bis(salicylic acid) by heating the appropriate bis(salicylic acid) with the appropriate fluorinated alcohol in the presence of dilute sulfuric acid under reflux. In order to obtain adequate yields, the reflux time is preferably greater than about 24 hours, more preferably greater than about 48 hours. After heating, the mixture is neutralized with sodium bicarbonate. The solution is purified by filtering, washing the filtered solid with aqueous sodium bicarbonate solution, and recrystallizing the fluorinated bis(salicyalte) from a mixture of acetone and water.

The monomers of this invention may be polymerized via conventional bisphenol A polycarbonate interfacial or solution processes. See, for example, Ferdinand Rodriquez, *Principles of Polymer Systems*, 2nd edition, Hemisphere Publishing Corporation, N.Y., N.Y., 1982, page 433; Fred Billmeyer, *Textbook of Polymer Science*, 2nd edition, John Wiley and Sons, N.Y., N.Y., 1971, page 456; and Kirk-Othmer *Encyclopedia of Chemical Technology*, 3rd edition, John Wiley and Sons, N.Y., N.Y., 1982, Vol. 18, pages 479–494; the relevant portions incorporated herein by reference.

SPECIFIC EMBODIMENTS

The example is provided for illustrative purposes only and is not intended to limit the scope of the invention or the claims.

EXAMPLE 1

Synthesis of Di-(2,2,2-trifluoroethyl)-5,5'-methylenebis-(salicylate)

A mixture containing about 35 grams of 5,5'-methylenebis(salicylic acid), about 150 milliliters of 2,2,2-trifluoroethanol, and about 5 milliliters of 96 percent sulfuric acid is refluxed for a total of about 64 hours, using a cycle of about 8 hours of heating and about 16 hours of standing at ambient temperature. The resultant mixture is poured into about 1200 milliliters of water and about 30 grams of sodium bicarbonate is then carefully added to neutralize the acids. The solution is filtered on a coarse frit and the solid washed with about 100 milliliters of saturated sodium bicarbonate solution and about 100 milliliters of water. The residue is recrystallized from a mixture of acetone and water, resulting in about 0.46 grams of di-(2,2,2-trifluoroethyl)-5,5'-methelenebis(salicylate) for about a 0.8 percent yield.

The melting point of the isolated compound is determined to be about 155° to 158.7° C.

Gas chromatographic analysis is conducted using TC detector with a 6 foot long, 2 millimeter internal diameter column packed with 10 percent SP-2100 on 100-120 mesh Supelcoport using helium as a carrier gas at 30 milliliters/minute. The injector and detector temperatures are at about 250° C. The oven is programmed at a temperature of about 100° C. for about 2 minutes, then heated at a rate of about 16° C./minute to about 250° C. held for about 16 minutes. A dilute solution of the synthesized compound in acetone shows one peak at 13.79 minutes. A dilute solution in N,O-bis(trimethylsilyl)acetamide shows a major peak at about 18.14 minutes and minor peaks at about 7.32, 15.32, and 16.52 minutes.

Analysis by infrared spectroscopy conducted in mineral oil indicates peaks at frequencies of 3160 m br, 1690 s, 1622 w, 100 w, 1492 s, 1350 m, 1301 vs, 1253 m, 1212 s, 1167 vs, 1026 m, 970 m, 859 m, 793 m, 654 m cm-1 with vs=very strong, s=strong, m=medium, w=weak, br=broad intensities.

Analysis by H1 NMR conducted at 80 MHz in acetone-$d_6$ gives 10.12$\delta$, s, O-H; 7.81$\delta$, d, J=2.0 Hz, H3; 7.47$\delta$, d.d, J=2.0, 8.5 Hz, H5; 6.95$\delta$, d, J=8.5 Hz, H6; 4.98$\delta$, q, J=8.6 Hz, —CH$_2$ coupled to CF$_3$; 4.93$\delta$, s, Ar—CH$_2$.

What is claimed is:

1. The fluorinated bis(salicylate) corresponding to the formula:

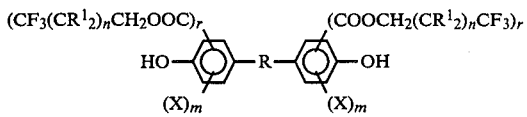

wherein
R is a $C_{1-18}$ divalent hydrocarbon radical, a $C_{1-18}$ divalent inertly substituted hydrocarbon radical, or a $C_{1-18}$ divalent halocarbon radical;
R$^1$ is independently in each occurrence a hydrogen or fluorine;
X is independently in each occurrence hydrogen, a halogen, a $C_{1-3}$ alkyl, a $C_{1-3}$ haloalkyl, or a nitrile;
m is independently in each occurrence an integer between 0 and 3 inclusive;
n is independently in each occurrence an integer between 0 and 6 inclusive; and
r is independently in each occurrence an integer between 1 and 4 inclusive.

2. The bis(salicylate) of claim 1 wherein R is a $C_{1-6}$ divalent hydrocarbon radical, a $C_{1-6}$ divalent inertly substituted hydrocarbon radical, or a $C_{1-6}$ divalent halocarbon radical.

3. The bis(salicylate) of claim 2 wherein R is a $C_{1-6}$ divalent hydrocarbon radical or a $C_{1-6}$ divalent fluorocarbon radical.

4. The bis(salicylate) of claim 3 wherein R is a $C_{1-6}$ divalent aliphatic hydrocarbon radical.

5. The bis(salicylate) of claim 4 wherein R is a $C_{1-3}$ divalent aliphatic hydrocarbon radical.

6. The bis(salicylate) of claim 5 wherein R$^1$ is independently in each occurrence fluorine.

7. The bis(salicylate) of claim 6 wherein X is independently in each occurrence hydrogen, chlorine, bromine, fluorine, methyl, ethyl, trifluoromethyl, or nitrile.

8. The bis(salicylate) of claim 7 wherein X is hydrogen, fluorine, methyl, ethyl, or trifluoromethyl.

9. The bis(salicylate) of claim 8 wherein X is hydrogen, fluorine, or methyl.

10. The bis(salicylate) of claim 9 wherein m is independently in each occurrence an integer between 2 and 3 inclusive.

11. The bis(salicylate) of claim 10 wherein n is independently in each occurrence an integer between 0 and 3 inclusive.

12. The bis(salicylate) of claim 11 wherein r is independently in each occurrence an integer between 1 and 2 inclusive.

* * * * *